United States Patent [19]
Yousefian

[11] Patent Number: 5,829,970
[45] Date of Patent: Nov. 3, 1998

[54] MOLAR DISTALIZATION APPLIANCE AND METHOD

[75] Inventor: Joseph Z. Yousefian, Bellevue, Wash.

[73] Assignee: Pro-Orthoappliance Corporation, Bellevue, Wash.

[21] Appl. No.: 639,291

[22] Filed: Jan. 16, 1996

[51] Int. Cl.$^6$ .................................................. A61C 7/00
[52] U.S. Cl. .............................................. 433/7; 433/21
[58] Field of Search .................................... 433/7, 18, 21

[56] References Cited

U.S. PATENT DOCUMENTS

| | | | |
|---|---|---|---|
| 4,468,196 | 8/1984 | Keller | 433/7 |
| 5,002,485 | 3/1991 | Aagesen | 433/7 |
| 5,022,855 | 6/1991 | Jeckel | 433/18 |
| 5,064,370 | 11/1991 | Jones | 433/21 |
| 5,324,196 | 6/1994 | Magill . | |
| 5,401,168 | 3/1995 | Magill . | |

OTHER PUBLICATIONS

Rondeau, B.H.M. "The Pendulum Appliance," *The Functional Orthodontist* 11:5–10 (1994).

*Primary Examiner*—Cary E. O'Connor
*Attorney, Agent, or Firm*—Christensen O'Connor Johnson & Kindness PLLC

[57] ABSTRACT

A method and apparatus for the distal movement of the molars, bicuspids and canines. A palate plate (10) is molded to the palate and attached to the teeth. The appliance also includes molar band attachments (16) that are attached to the palate plate by a spring-loaded wire (12). The spring (13) creates a distal force on the molars. The bicuspids are securely attached to the palate molar, therefore creating a distal movement of only the molars. Once the distal movement of the molars is complete, the bicuspids are detached from the palate plate (10) allowing for bicuspid distal movement.

5 Claims, 3 Drawing Sheets

MOLAR DISTALIZATION APPLIANCE AND METHOD

FIELD OF THE INVENTION

The present invention relates generally to orthodontic appliances, and more particularly to appliances used for molar distalization.

BACKGROUND OF THE INVENTION

Orthodontists and dental researchers are constantly searching for new and improved ways to correct the problem of malpositioning, commonly known as overcrowding or overlapping of teeth. In the past, many different methods have been used in order to alleviate this overlapping. One method that has been utilized by orthodontic practitioners is that of molar distalization.

The process of molar distalization is designed to move the molars in the posterior direction in the mouth to allow room for the other teeth. When designing a product to perform this distalization, one must consider two important factors. The first is how to make a product that performs this molar distalization in the most efficient manner possible. The second factor is how to make a product that is functional for the user as well as cosmetically appealing without inhibiting the distalization process.

One molar distalization device that is on the market today is referred to as the "Magill Sagittal" device, manufactured by Universal Dynamics, Inc., Minneapolis, Minn. The Magill Sagittal device includes bands mounted on the first bicuspids and second molars. The bands are coupled on the buccal side by a drive tube assembly disclosed in U.S. Pat. No. 5,401,168 that exerts a linear spreading force on the coupled teeth and by a stabilizing bar on the lingual side. The first bicuspid is also anchored to a small palate plate that covers the palate between the canines. The Magill Sagittal suitably performs the distalization process, yet suffers from several undesirable features. This device has insufficient palate coverage, and thus fails to isolate the first bicuspids and other anterior teeth from the distalization force due to inadequate anchorage. This force on the anterior teeth results in what is an undesirable anterior movement of the incisors, excepting those cases in which protraction of the anterior teeth is needed, as well as less of the desired posterior movement of the molars. Another undesirable feature is that the Magill Sagittal device is attached to the teeth by multiple obtrusive bands on each side of the mouth. The drive tube assemblies and stabilization bars of the device may be found uncomfortable and cosmetically unappealing by the patient. Maximum distalization in full adult dentition requires distalizing the second molars first, thus two sets of appliance are necessary to fit second molars and first molars. Simple adjustments require removal of all four bands. This wastes chairside time and risks fracture of teeth during debanding.

Another conventional distalization device is a Pendulum Appliance, disclosed in B. Rondeau, "The Pendulum Appliance," *The Functional Orthodontist,* Volume 11, Number 1, January/February 1994, pp. 5–12. This appliance includes a large palate plate that is anchored by bands on the first bicuspids or by wires bonded to the occlusal surfaces of the first and second bicuspids. Pendulum springs are connected between the posterior of the palate plate and bands on the first molars. The pendulum appliance also suffers from certain disadvantages. Due to the nature of the pendulum springs which are of constant length, the maxillary molars have a tendency to tip lingually when distalized. In order to compensate for this shortcoming, the patient must periodically return to the orthodontist in order to lengthen the pendulum spring and help prevent the unwanted lingual tipping. Another drawback of this appliance is that the force of movement is transmitted from the palate plate to the crown of the molar. This results in movement of the molar crown without a proportionate movement of the molar root. This causes the molar to tip dorsally. If not adjusted correctly, the pendulum spring becomes distorted and torqued and when inserted into the sheath of the molar, can result in undesirable rotation or torquing of the molars. While the device can be anchored by wires bonded to the occlusal surfaces of the bicuspids, the need to periodically remove the device to reactivate the springs makes anchoring this device unsuitable in practice. The painstaking maintenance of this device becomes inconvenient, time-consuming and ultimately very expensive for the patient.

SUMMARY OF THE INVENTION

The present invention provides an improved orthodontic appliance for use in molar distalization. The appliance includes left and right molar bands each securable around the patient's left and right molars, first or second molars. A support plate of the appliance includes devices used for anchoring the plate to the anterior teeth. Left and right spring assemblies connect the support plate to the left and right molar bands. Each spring assembly includes an elongate rod having a posterior end connected to the corresponding left or right molar band and an anterior end slidably secured to the support plate. A compression spring is received on the rod to produce a spring force between the palate plate and the left and right molar bands. The term "anterior teeth" refers essentially to the bicuspids, canines, and incisors.

One improvement is that the support plate is a palate plate conformed to the contour of a patient's upper palate and the appliance is designed to move only those teeth that need to be moved. This appliance is also improved to require less maintenance and parts, therefore less cumbersome and more cosmetically appealing for the patient. Still further it is less expensive because it requires less hardware and maintenance.

The present invention initially creates posterior movement of the second and first molars while maintaining the position of the anterior teeth. Once the molars have been moved to their desired position, the bicuspids are allowed to move independently in a posterior direction in order to close the gap which was created by the posterior movement of the molars. Adjustments of the appliance are made without removal from the patient's mouth. The spring assembly is separately removable for adjustment without damage or discomfort to the patient.

The linear forces on the molars in this device create a positive movement of the tooth, therefore preventing the tooth from tipping dorsally. Further, the anchoring of the palate plate to the teeth along with the singular connection to the molar band create a device that is less obtrusive to the patient and therefore more cosmetically desirable. The singular connection point on the lingual side of the molar band also allows for connection of various devices, such as braces or headgear, to the buccal side of the band.

Another improvement is that the support plate is a lingual incisor plate conformed to the lingual side of the incisors. The lingual incisor plate is secured to the incisors by a bar that secures a labial plate to the labial side of the incisors while each end of the bar is secured to the corresponding end of the lingual incisor plate.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
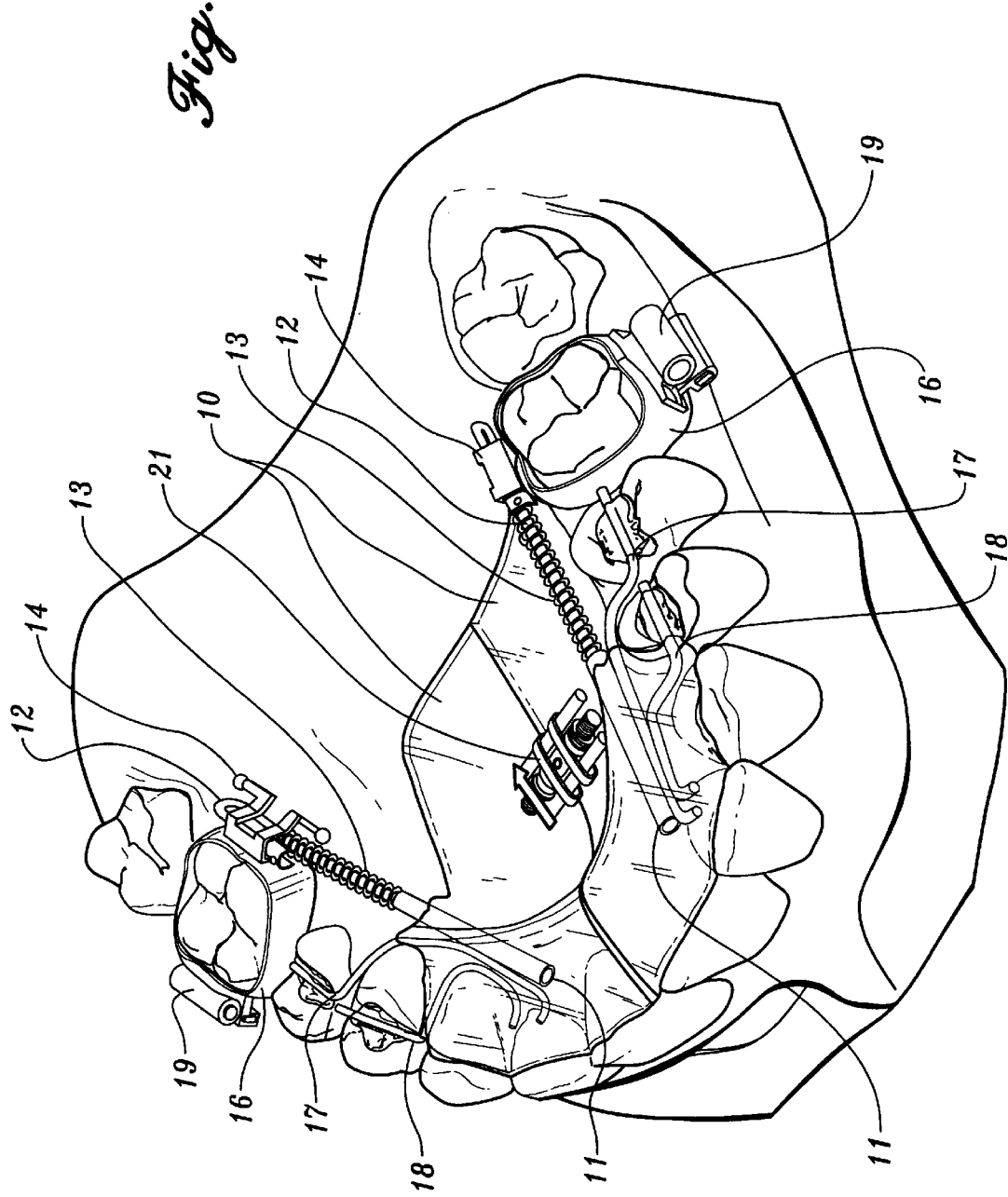
FIG. 1 illustrates a perspective view of a preferred embodiment of the orthodontic appliance in accordance with the present invention being worn on the upper palate of a patient.

FIG. 1 illustrates an embodiment of an appliance constructed in accordance with the present invention. FIG. 1 illustrates the upper palate of a patient with the appliance resting on the palate and attached to the patient's teeth. The appliance includes an acrylic palate plate 10 that is custom fitted to the patient's palate. The palate plate 10 consists of left and right symmetrical halves. When the plate is formed, two stainless steel wires 17, 18 and one stainless steel sheath 11 are embedded into each half A conventional spreader device 21 is also inserted into the plates at the top inner portion of each half. The spreader device 21, used for expansion, connects the two halves of the plate and maintains their relative spacing.

When in place, the plate 10 extends from the anterior portion of the palate directly behind the incisors, to the posterior portion of the palate approximately in line with the mesial side of the first molars. The anterior half of the palate plate extends laterally from the distal side of the left canine to the distal side of the right canine, maintaining a bite plane of adequate width. The posterior half of the palate plate 10 is sufficiently wide enough to contain the spreader 21 and to support the force of the distalization.

A connection between the palate plate 10 and a molar is established during installation of the appliance. First, two metal sheaths 11 are embedded into the plate 10. The sheaths 11 are located on the lower, outward portion of each half of the plate 10, and oriented in an anterior to posterior direction angled downwardly to the lingual side of the first molars. Each sheath 11 is open at the posterior end. The sheath opening is located approximately at the edge of the plate slightly higher than the gum line on the lingual side of the first bicuspid. The location of the sheath depends upon the shape of the patient's palate and the location of the anterior and posterior teeth.

Standard removable metal molar bands 16 are securely strapped to the first molars. Each molar band 16 has a clasp 14 attached to the lingual side of the molar band 16. Each band 16 also has a multiple connecting piece 19 attached to its buccal side. The multiple connecting piece 19 is attachable to various conventional orthodontic devices such as braces or headgear.

A 0.038–0.040 inch diameter stainless steel wire 12 is first inserted into a spring 13, then into each sheath 11, and finally connected to the clasp 14. Wire 12 extends posteriorly towards the molars approximately parallel to the lingual side of the molars. The posterior end of wire 12 extends to the molar band clasp 14 where it is secured. Wire 12 angles in a downward direction directly from sheath 11 to the molar band clasp 14. When wire 12 is in place, spring 13 maintains contact at one end with the open end of the sheath and on the other end to the molar band clasp 14. The noted diameter is found to be suitable, but other dimensions may be utilized with a corresponding change in sheath size.

In order for this invention to function efficiently, the initial placement of the sheaths 11 is very important. Due to differences in palate shape and location of teeth, each patient requires a uniquely shaped device. Therefore, each sheath 11 must be inserted such that wire 12 makes a direct path to the band clasp 14. This placement ensures that the force created by the spring transfers directly to the molar.

The spring 13 is large enough to create the desired expansion forces between the palate, via the plate, and the molars, via the bands. The spring creates an expanding linear force. The opposing objects are the banded molars and the palate whereon the palate plate rests in combination with the anterior teeth. The palate, in combination with the anterior teeth, is more stable than the molars. The force from the spring will force the molars into the desired distalization motion.

First cement bars 17 are securely embedded in the palate plate next to and exterior to the sheaths 11. The first cement bars 17 extend out of the plate and over the top of the second bicuspids in the direction of the mesial to the distal side of the tooth. These bars must extend far enough over the teeth in order to allow for a secure cement bond. These bars are sufficiently pliable to allow for the adjustment at the crown of the teeth while maintaining sufficient support for the teeth once cemented to counter any possible movement of the teeth.

Second cement bars 18 are also securely embedded in the palate plate 10. The cement bars 18 project from the plate between the canine and first bicuspid. The cement bars 18 are located over the first bicuspids in the mesial to distal direction and cemented to these teeth. The cement bars 18 are secured to the teeth in the same manner as the first cement bars 17 and are made of the same material.

The spring force acting on the bands 16 on the first molars will drive the first and second molars distally. When the proper movement of the molars is complete, the springs 13 on the wires are locked by cementing the springs 13 to the wires 12. This ensures that no more expansion of the springs or movement of the molars takes place. The first cement bars 17 connecting the second bicuspids are then detached. This allows the second bicuspids to naturally move towards the molars under the force of connective tissues.

When the proper movement of the second bicuspids is complete, the second cement bars 18 are detached from the first bicuspids. After the detachment, the plate is trimmed back far enough to expose the canines. Then the second cement bars 18 are bent to a position over the canines and cemented thereto. This allows the first bicuspids to naturally move towards the molars.

The attachments to the first and second bicuspids are not limited to wires but could also be tooth bands similar to those used on the molars. However, the use of wires is preferred because they are less obtrusive to the patient and more easily maintained by the doctor.

To create a lateral force on the teeth, a spreader device 21 is built into each half of the palate plate. When activated, the spreader 21 expands the palate plates laterally, thus putting pressure on the teeth. The force created by the spreader 21 aids in the correction of malpositioning. Any outward lateral movement of the teeth creates more room for the teeth.

When all tooth movement is complete, the apparatus is removed. If the patient's molars need more care, the molar bands can be left in place. As described previously, the molar bands 16 have a multiple connecting piece 19 attached to their buccal side which allows for the attachment of various other types of orthodontic devices.

Figure 3:
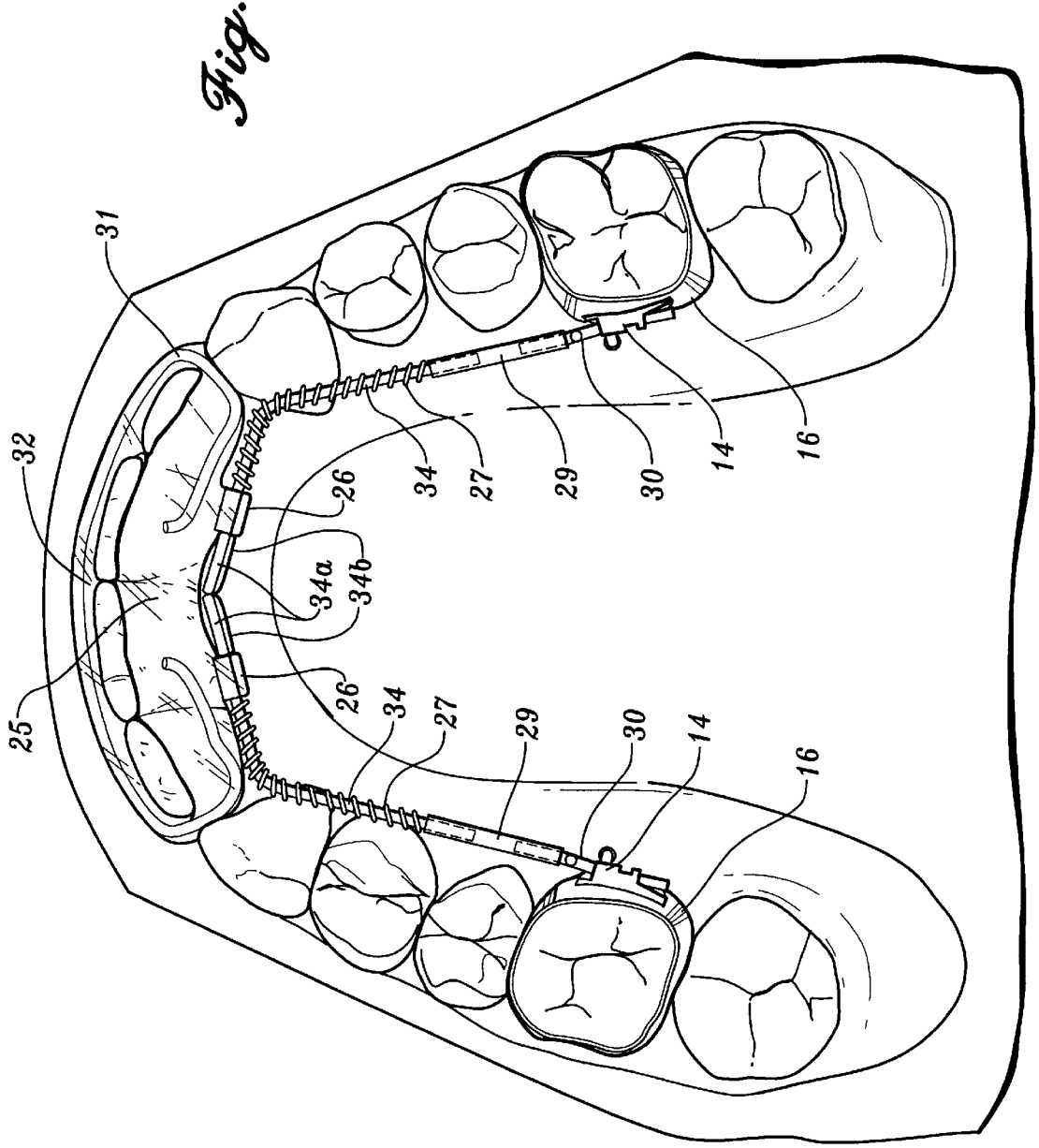
FIG. 3 provides a plan view of the bottom of another embodiment of the appliance, viewed looking upwardly along the appliance when installed on the upper palate of the patient.

FIG. 3 illustrates another embodiment of an orthodontic appliance constructed in accordance with the present invention. An acrylic plate 25 located on and molded about the lingual side of the central and lateral incisors extends approximately from the gumline of the incisors to the top of the incisors and from approximately between the left canine and left lateral incisor to approximately between the right canine and the right lateral incisor. The plate 25 is much smaller than the previously described plate 10 of the appliance of FIG. 1, and is suitable for use when protraction of the anterior teeth is desired. Referring still to FIG. 3, when the acrylic plate 25 is formed, both ends of a stainless steel wire 31 and two stainless steel sheaths 26 are embedded at the lateral ends of the acrylic plate 25. The embedded sheaths 26 and the ends of wire 31 are positioned longitudinally in the acrylic plate 25 and are approximately equidistant from an anterior to posterior centerline of the acrylic plate 25. The stainless steel wire 31 extends out of one end of the acrylic plate 25, bends to pass between the adjacent lateral incisor and canine, follows a path along the labial side of the incisors, and bends back between the other lateral incisor and canine, to an embedded position within the other end of the acrylic plate 25. A labial acrylic mold 32, molded around the labial side of the incisors, encases the wire 31 as it travels along the labial side of the incisors.

Figure 2:
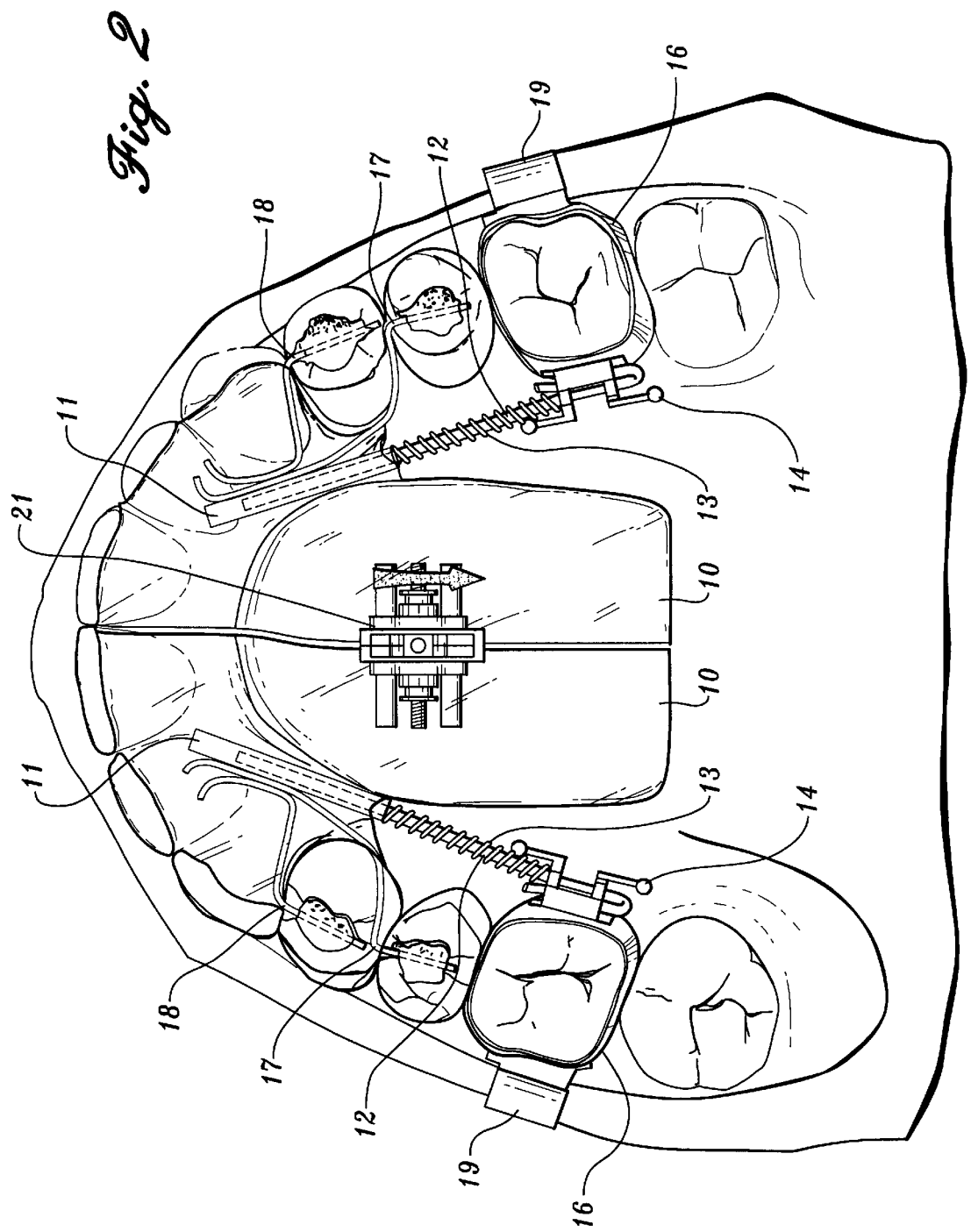
FIG. 2 provides a plan view of the bottom of the appliance of FIG. 1, viewed looking upwardly on the appliance when installed on the upper palate of the patient.

The embodiment of FIG. 3 contains the same molar bands 16, clasps 14, and similar but shorter stainless steel wires 30 connected to the clasps 14 as shown in the previous embodiment of FIGS. 1 and 2. Each stainless steel wire 30 projects in the anterior direction from the corresponding band clasp 14 a short distance and is secured within the inside of one end of a corresponding tubular stainless steel sheath 29. The tubular sheath 29 travels in an anterior direction along the lingual side of the bicuspids. The other end of the tubular sheath 29 is located approximately at a position between the first and second bicuspids.

On each side of the appliance, a bent stainless steel wire 34 is inserted into a coil spring 27, is slidably inserted at one end into the corresponding tubular sheath 29, and at the other end is slidably inserted into the embedded sheath 26 of the acrylic plate 25. When the orthodontic appliance of this embodiment is installed, the spring 27 maintains contact at one end with the open end of the tubular sheath 29, and at the other end with the embedded sheath 26. The stainless steel wire 34 travels in a path along the lingual side of the bicuspids from the tubular sheath 29, then bends inward approximately at the canines for insertion into the embedded sheaths 26. The forces due to the spring are exerted in two directions, to achieve two different purposes. The spring can accordingly be configured to exert both an anterior-to-posterior distalizing force upon the molars via the band clasps 16 and a protraction force on the incisors, and a lateral expansion force, due to the bend in the wire 34 at the anterior portion of the palate, for spreading of the arch.

The appliance also includes structure permitting selective limitation of the degree of arch spread. Referring still to FIG. 3, the anterior end of each wire 34 that is received within the corresponding anterior sheath 26 is bent in the shape of a "U". Each wire thus has a long leg 34a and a short leg 34b that is received within the sheath 26. The length of the short leg 34b is selectively adjusted by snipping the wire 34 with a wire cutter. During use, expansion of the spring 27 as the arch spreads causes the bent end of the wire 34 to withdraw from the sheath 26. This process continues until the tip of the short leg 34b is even with the side of the sheath 26 facing the adjacent canine. At this point, the spring 27 begins to bear on the tip of the short leg 34b, rather than the sheath 26, preventing further withdrawal of the wire 34 from the sheath 26, and thereby limiting spread of the patient's arch to this predetermined extent.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An orthodontic appliance for treating distalization of malposed molars of a patient, comprising:
    (a) an upper plate, wherein said upper plate is a palate plate conformed to a patient's upper palate;
    (b) left and right molar bands each securable around corresponding left and right molars of the patient;
    (c) left and right bicuspid wires extending from the palate plate, each securable to corresponding left and right second bicuspids of the patient to anchor the upper plate to the anterior teeth within the patient's mouth; and
    (d) left and right linear spring assemblies, each linear spring assembly including an elongated rod having a posterior end connected to a corresponding left or right molar band and an anterior end connected to the upper plate, at least one of the anterior and posterior ends being slidably connected to the corresponding molar band or upper plate, and a compression spring received on the rod to produce a spring expansion force between the upper plate and the left and right molar bands, wherein said anterior end of said rod is slidably received within a tubular sheath secured to said palate plate.

2. The orthodontic appliance of claim 1, wherein said sheath is embedded within said palate plate.

3. An orthodontic appliance for treating distalization of malposed molars of a patient, comprising:
    (a) an upper plate, wherein said upper plate is a palate plate conformed to a patient's upper palate;
    (b) left and right molar bands each securable around corresponding left and right molars of the patient;
    (c) a first set of left and right bicuspid wires extending from the palate plate, each securable to corresponding left and right second bicuspids of the patient to anchor the upper plate to the anterior teeth within the patient's mouth;
    (d) a second set of bicuspid wires each securable to corresponding left and right first bicuspids of the patient; and
    (e) left and right linear spring assemblies, each linear spring assembly including an elongated rod having a posterior end connected to a corresponding left or right molar band and an anterior end connected to the upper plate, at least one of the anterior and posterior ends being slidably connected to the corresponding molar band or upper plate, and a compression spring received on the rod to produce a spring expansion force between the upper plate and the left and right molar bands.

4. An orthodontic appliance for treating distalization of malposed molars of a patient, comprising:
    (a) an upper plate, wherein said upper plate is a lingual incisor plate conformed to the lingual side of a patient's incisors;

(b) left and right molar bands each securable around corresponding left and right molars of the patient;

(c) means for anchoring the upper plate to the anterior teeth within the patient's mouth; and (d) left and right linear spring assemblies, each linear spring assembly including an elongated rod having a posterior end connected to a corresponding left or right molar band and an anterior end connected to the upper plate, at least one of the anterior and posterior ends being slidably connected to the corresponding molar band or upper plate, and a compression spring received on the rod to produce a spring expansion force between the upper plate and the left and right molar bands, wherein said anterior end of said rod is slidably received within a sheath laterally secured to said lingual incisor plate thereby producing a lateral expansion force and a longitudinal expansion force.

5. The orthodontic appliance of claim 4, wherein said posterior end of said rod is slidable received within a sheath secured to the corresponding molar band.

\* \* \* \* \*